United States Patent [19]

Kasama et al.

[11] 4,318,696
[45] Mar. 9, 1982

[54] IMPLANT ARTIFICIAL DENTURE

[76] Inventors: Katsumi Kasama; Toru Kasama, both of 2-3, Minamirinkan 2-chome, Yamato-shi, Kanagawa-ken, Japan

[21] Appl. No.: 101,856

[22] Filed: Dec. 10, 1979

[30] Foreign Application Priority Data

Dec. 14, 1978 [JP] Japan .................. 53/15373
Apr. 26, 1979 [JP] Japan .................. 54/50929
Jun. 16, 1979 [JP] Japan .................. 54/75176

[51] Int. Cl.³ .............................................. A61C 8/00
[52] U.S. Cl. ................... 433/173; 433/169; 433/220; 433/201; 433/222
[58] Field of Search ............... 433/172, 173, 174, 175, 433/176, 164, 220, 169

[56] References Cited

U.S. PATENT DOCUMENTS

| | | | |
|---|---|---|---|
| 1,193,329 | 8/1916 | Withycombe | 433/169 |
| 3,618,212 | 11/1969 | Weissman | 433/173 |
| 3,827,145 | 8/1974 | Richards | 433/175 |
| 3,955,280 | 5/1976 | Sneer | 433/169 |
| 4,178,686 | 12/1979 | Riess | 433/173 |
| 4,215,986 | 8/1980 | Riess | 433/173 |

*Primary Examiner*—Robert Peshock
*Attorney, Agent, or Firm*—Cushman, Darby & Cushman

[57] ABSTRACT

The present invention provides an implant artificial denture comprising an intra-ossal implant implanted in the jaw, an elastic material fitted over the head of the intra-ossal implant, a crown of tooth and, if required, a receiver fitted over the head of the intra-ossal implant, wherein the receiver prevents the elastic material from falling off when chewing and masticatory pressure or shock is applied thereto and the elastic material absorbs the chewing and masticatory pressure or shock applied thereto to prevent lesion of the surrounding tissue, and further provides an implant artificial denture equipped with a chewing load limit sensing device incorporated therein, which aids in preventing lesion of the surrounding tissue.

30 Claims, 9 Drawing Figures

IMPLANT ARTIFICIAL DENTURE

BACKGROUND OF THE INVENTION (1) Field of the Invention

This invention relates to an implant artificial denture, and more particularly an implant artificial denture which can prevent lesion of the surrounding tissue especially by improving the upper structure thereof.

(2) Description of the Prior Art

Attempts of restoring the function of a decidual or extracted tooth by a so-called implant artificial denture have increasingly been made. For providing an implant artificial denture, an intra-ossal implant or an intra-ossal implant in the tooth (hereinafter referred to as simply intra-ossal implant) is impacted in the jaw to employ it as the dental root, and an upper structure is fitted thereover.

Accordingly, many proposals for artificial dentures, particularly for material, shape, etc. of artificial dentures have been made. Now an improvement in the intra-ossal implant is being made to such an extent that it has such a mechanical strength as to withstand a high masticatory pressure.

However, fixing of the intra-ossal implant in the jaw caused other clinical problems.

In the natural tooth, the chewing and masticatory pressure or shock is absorbed by the absorbing action of the periodontal membrane. Contrary thereto, in an implant artificial denture, the pressure and shock applied to the upper structure are applied directly to the jaw, which induces inflammation of tissue as well as the dissolution and uptake of bone in the neighbourhood of the interface between the intra-ossal implant and the jaw tissue. Therefore, it is usually necessary in an implant artificial denture to make the masticatory surface smaller and smoother so that the pressure or shock applied to the dental root may not be so high, and to reduce the masticatory force by other means, which results in a state at which complete chewing is greatly sacrificed.

Thus the upper structure of conventional implant artificial dentures was at such a state as to be much improved.

Lightening of the load imposed on the artificial denture by fixing it to the adjacent healthy teeth results in injuring the healthy teeth.

In the natural tooth, a shock as in biting a solid foreign body and abnormally high chewing pressure are absorbed by the action of the periodontal membrane, and an excessive pressure or abnormally high shock applied to the tooth or the jaw during chewing or in a state where a biting force is applied thereto is naturally transmitted to cerebral nerves to be controlled accordingly.

However, an implant artificial denture can not provide all the abilities the natural tooth posseses, and has great drawbacks to be solved.

Particularly, the implant artificial denture neither has the periodontal membrane the natural tooth posseses, nor posseses any sensing ability for the transmission of masticatory pressure.

That is, no transmission of masticatory pressure to cerebral nerves is made in the case of the implant artificial denture, so that the pressure and shock applied to the upper structure thereof are applied directly to the jaw, which results in inducing inflammation of tissue as well as the dissolution and uptake of bone in the neighbourhood of the interface between the intra-ossal implant and the jaw tissue, and causing lesion of the implant artificial denture, the surrounding tissue, the jaw joint and the like. These are serious drawbacks of implant artificial dentures.

However, it is generally impossible to join an implant artificial denture to the sense organs of the cerebral nerves. Accordingly, it is necessary to sense the danger due to abnormally high mechanical shock with a stimulation instead of relying upon an exitation of the pain sense which occurs in the case of the natural tooth as described above.

Therefore, the inventors studied the method of sensing the limit of chewing force applied to implant artificial dentures by incorporating a stimulation-producing device in the upper structure of an implant artificial denture, and by sensing the stimulation produced by the device through the internal ear.

It was proved that an abnormally high pressure or shock is sensed and may be voluntarily controlled by the use of an echo device fitted inside a crown of tooth to sense an abnormally high pressure or shock to the patient through the internal ear.

SUMMARY OF THE INVENTION

An object of the present invention is to provide an implant artificial denture having a chewing ability similar to that of a natural tooth.

Another object of the present invention is to provide an implant artificial denture free of unfavorable phenomena in the neighbourhood of the interface between an intra-ossal implant and the jaw.

Another object of the present invention is to provide an implant artificial denture most suited for conditions of a region where an intra-ossal implant is implanted, by selecting an elastic material to be fitted depending on the biting force expected to be applied thereto.

A still further object of the present invention is to provide an implant artificial denture which can adjust its conditions depending on the change of tissue in the region where an intra-ossal implant was implanted by operation, or the change of the surrounding tissue after having the implant artificial denture in place for a long period of time.

Another object of the present invention is to provide an implant artificial denture which can provide, independently, a satisfactory function without injuring adjacent healthy teeth.

Another object of the present invention is to provide an implant artificial denture incorporating a novel chewing load limit sensing device in the upper structure thereof.

A further object of the present invention is to provide an implant artificial denture having a novel upper structure which prevents damage to the implant artificial denture and the surrounding tissue by sensing the chewing load limit.

A still further object of the present invention is to provide an implant artificial denture having an elastic material fitted between its intra-ossal implant and its crown to absorb the masticatory pressure and shock, and having a chewing load limit sensing device depending on the elastic material used and other conditions for the application of the artificial denture.

DETAILED DESCRIPTION OF THE PREFERRED EMBODIMENTS

Figure 1:
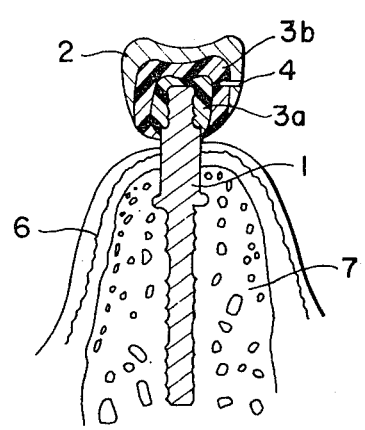
FIG. 1 is a longitudinal cross sectional view of an implant artificial denture showing an embodiment of the present invention.

According to the implant artificial denture of the present invention, a crown of tooth is not fixed directly to the head of the intra-ossal implant, but is fixed thereto through the intermediacy of an elastic material.

The elastic material is made of a material with a coefficient of elasticity suited for the biting force applied to the tooth usually at that location, with the result that the biting force is dissipated, that the shock on the implant root is absorbed, and that the implant and the jaw tissue are found to be protected.

The elastic material can be exchanged between immediately after the implant is implanted and after the wound of the bone was cured, and the upper structure of the implant artificial denture having an elastic material with such a broad range of coefficient of elasticity as to be suited for individual difference is thereby provided.

According to the implant artificial denture of the present invention, a receiver when fitted over the head of the intra-ossal implant increases the function and effect of the elastic material fitted thereover and makes it possible to provide an increased function and a greater effect with a smaller amount of the elastic material compared with the case where no receiver is fitted.

According to the implant artificial denture of the present invention, in which an elastic material is fitted between the head of the implant and the crown of tooth, a chewing load limit sensing device comprising a diaphragm incorporated in the elastic material and a tympanic cavity necessary for temporary oversion of the diaphragm is incorporated in the upper structure of the implant artificial denture.

An abnormally high pressure or shock during chewing or in biting causes inversion of the diaphragm to produce a bounding sound and vibration, which are effectively transmitted to the internal ear as a particular phenomenon in the cavity of the mouth.

Thus the patient can recognize the load limit of the chewing pressure or masticatory pressure and respond thereto to prevent various difficulties as described above, which were caused by a chewing pressure or masticatory pressure exceeding a certain level in the use of prior art implants.

That is, the present invention provides an implant artificial denture comprising an intra-ossal implant implanted in the jaw, an elastic material fitted over the head of the implant and a crown of tooth fitted over the elastic material.

The present invention also provides an implant artificial denture comprising an intra-ossal implant, a receiver fitted over the head of the intra-ossal implant, an elastic material fitted over the receiver and a crown of tooth fitted over the elastic material, the receiver having a supporting collar section integrally fitted thereto, which is shaped to be fitted over the elastic material.

This invention further provides an implant artificial denture comprising an intra-ossal implant, an elastic material fitted over the head of the intra-ossal implant, a crown of tooth fitted over the elastic material, and, if required, a receiver fitted over the head of the intra-ossal implant and a chewing load limit sensing device fitted in the elastic material.

The chewing load limit sensing device comprises an elastic diaphragm and a tympanic cavity. The elastic diaphragm is incorporated between the tip of the head of the implant and the back side of the crown of tooth in the axial direction of the implant in such a manner that it is fitted in the vertical direction to the implant axis, that the center thereof coincides with that of the implant axis, that the both ends of the diaphragm are fixed in the elastic material and that an everting portion of the diaphragm is shaped to form a gently curved surface to the head of the implant and temporarily everts under a chewing pressure exceeding a certain limit to produce a bounding sound.

The tympanic cavity has a cavity necessary for the eversion of the elastic diaphragm.

The basic intra-ossal implant according to the present invention may be arbitrarily selected from known implants with various shapes, and there are no limitations for its shape and structure.

The material used for the intra-ossal implant may be selected from those which have sufficient mechanical strength and durability, and which will fit well with the jaw tissue.

Examples of the material used for the intra-ossal implant of the present invention include a single crystal of alumina, magnesia, titanium carbide or the like, ceramics such as sintered material, metals such as titanium, cobalt, chromium and the like, resin carbides and a composite material thereof, preferably a material obtained by sintering ceramics on the surface of the implanted portion of a metal implant.

Examples of the material used for the crown of tooth of the present invention may include dental material conventionally used such as ceramics, synthetic resin, a simple substance or alloy of metal, and the like.

The elastic material used in the present invention must have a thickness enough to support the crown of tooth and absorb the pressure or shock applied thereto. The elastic material of used in present invention must have a suitable coefficient of elasticity corresponding to the masticatory pressure so that it may support the crown of tooth without remarkable distortion against the masticatory pressure and absorb the masticatory pressure or shock.

Masticatory pressure differs individually and varies with age, hygienic condition and the position in the denture to which the pressure is applied, so that it is difficult to define as a whole, but generally the masticatory pressure produced by chewing consciously reaches above 60 kg/cm$^2$, sometimes above 100 kg/cm$^2$, and the chewing pressure produced by normal chewing is usually in the range of from 20 to 70 kg/cm$^2$.

The elastic material used in the present invention is required to compress to a desired degree in thickness when the above chewing pressure is applied thereto, and may be selected from those ranked depending on the coefficient of elasticity taking into consideration the shape, size, specific masticatory pressure, conditions of the jaw, and the like.

Immediately after the implant is subjected to operation, for example, an elastic material, which has a high coefficient of elasticity as to compress in the range of from 0.5 to 1 mm during chewing, is preferably used in order that a very low pressure may be applied to the root of the implant.

A sponge-like material with a certain hardness may temporarily be used. After the bone operation wound is healed, it is preferable to use such an elastic material one which compresses in the range of from 0.1 to 0.2 mm due to the normal masticatory pressure.

Thus the elastic material used preferably has a coefficient of elasticity as to compress appropriately according to the pressure applied thereto, for example, ranging from one resulting in a volumetric compression of about 1/50 under a pressure of 0.5 kg/cm$^2$ to one resulting in a volumetric compression of about 1/50 under a pressure of 100 kg/cm$^2$.

The elastic material may be fitted as a uniform single layer construction, preferably a multi-layer construction, for example, comprising a soft elastic material fitted over the head of the implant or the receiver and a rigid elastic material fitted over the soft elastic material.

In the case where a receiver is provided, the amount to be used of the soft elastic material can be less than that required in the case where a receiver is not provided.

The material used for the elastic material mentioned above may be a polymeric material which is exellent in non-susceptibility to water damage, shock resistance, and which has age resistance, wear resistance, resistance to deterioration, resistance to corrosion, is safe, etc. Examples of the polymeric material include silicone resin, nylon, fluoroplastics, vinyl resin, polyacrylic ester resin, polyolefin plastics, polyurethane plastics and the like.

The material for the soft elastic material surrounded completely by the receiver and the rigid elastic material may be in a wider range compared with that used for the rigid elastic material, which is not always surrounded completely by the receiver and the crown of tooth.

The receiver fitted over the head of the implant of the present invention is effective to increase the shock-absorbing function of the elastic material by ensuring support of the elastic material when a chewing or masticatory pressure is applied to the elastic material fitted thereover, and also is effective to increase the restoring ability when the pressure is released. The receiver may be made of a rigid material such as stainless steel.

The elastic diaphragm used in the chewing load limit sensing device of the present invention is in the form a thin plate with its temporarily everting portion shaped to form a gently curved surface to the head of the implant, and is of such an elasticity as to be everted the moment a chewing pressure exceeding a certain limit was applied thereto and to be restored, i.e. reverted, immediately after the pressure is released. The diaphragm used is usually thinner at the everting portion compared with both ends thereof.

The feeling of vibration and the sound produced by the temporary eversion of the elastic diaphragm are transmitted to the internal ear, which makes the patient recognize them to enable the patient to respond to the danger.

The elastic diaphragm is incorporated between the tip of the head of the implant and the back side of the crown of tooth in the axial direction of the implant in such a manner that it is fitted in the vertical direction to the implant axis and that the center thereof coincides with that of the implant axis.

Both ends of the elastic diaphragm of the present invention are fixed in the elastic material, preferably in the rigid elastic material where the elastic material comprises a soft elastic material layer and a rigid elastic material layer.

The everting portion of the elastic diaphragm of the present invention is usually shaped to form a gently curved convex surface to the head of the implant, and a spring device may be fitted thereto in order to ensure the restoration thereof after the bone operation wound heals.

As an embodiment of the spring device, a spring device for the restoration of the diaphragm may be fitted between the elastic diaphragm and the back side of the crown of tooth in the axial direction of the implant, which spring device comprises a spring, a spring receiver having a spring receiver screw section and a spring bearer both integrally fitted to the head thereof, and a spring receiver bearer.

As another embodiment of the spring device used in the chewing load limit sensing device of the present invention, which spring device comprises a spring, a spring bearer and a spring receiver, wherein the spring and the spring bearer are fitted between the tip of the head of the implant and the elastic diaphragm, the everting portion of which is shaped to form a curved concave surface to the head of the implant, and the spring receiver is fitted between the elastic diaphragm and the back side of the crown of tooth.

Stainless steel, for example, may be suitable as material for the spring receiver, the spring receiver bearer and the spring.

The tympanic cavity of the chewing load limit sensing device constitutes a cavity necessary for the temporary eversion of the elastic diaphragm and has an echo effect on the bounding sound produced by the temporary eversion of the elastic diaphragm. The tympanic cavity may be provided with an interstice open thereto and leading to the back side of the crown of tooth in the axial direction of the implant in order to enhance the echo effect of the bounding sound.

The space between the top surface of the everting portion of the elastic diaphragm and the tip of the head of the implant may preferably be less than about 3 mm along the longitudinal axis of the implant depending on the coefficient fo elasticity of the elastic material used.

This is true of the space between the top surface of the everting portion of the elastic diaphragm and the tip of the spring receiver in the case where the everting portion is shaped to form a curved concave surface to the head of the implant.

The component parts such as the receiver, the elastic material, the crown of tooth, the chewing load limit sensing device, and the like of the implant artificial denture of the present invention may be fixed with adhesive or the like, but preferably are fitted detachably from each other as hereinafter described in detail, so that the exchange or dental prosthesis thereof may be effected arbitrarily, which results in advantageous dental therapy as well as maintenance thereof.

For a relatively short period of time after the implant is implanted, an appropriately light shock applied to the implant root may be rather desirable for the healing and development of the surrounding tissue, but the healing and development are inhibited when the shock is too high, so that an appropriately soft elastic material may preferably be used.

When the intra-ossal implant has been fit in the jaw, after passage of a long period of time, namely, 1 to 3 months after the operation, the soft elastic material may be exchanged for an elastic material with a coefficient of elaticity corresponding to the normal masticatory pressure.

Moreover, it is also necessary to examine the conditions of the implant artificial denture and the surrounding tissue at appropriate intervals and, if required, to effect an exchange of the elastic material and the prosthesis of the crown of tooth.

The present invention will be further illustrated in detail by the following drawings.

Figure 3:
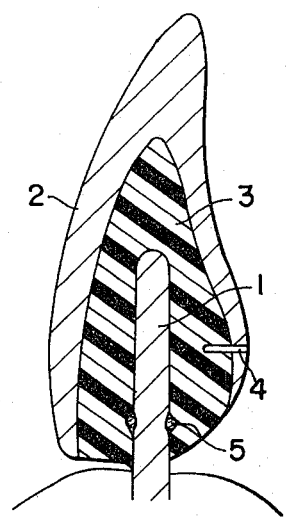
FIG. 3 is an enlarged cross sectional view of the upper structure of the implant artificial denture showing another embodiment of the present invention.
Figure 2:
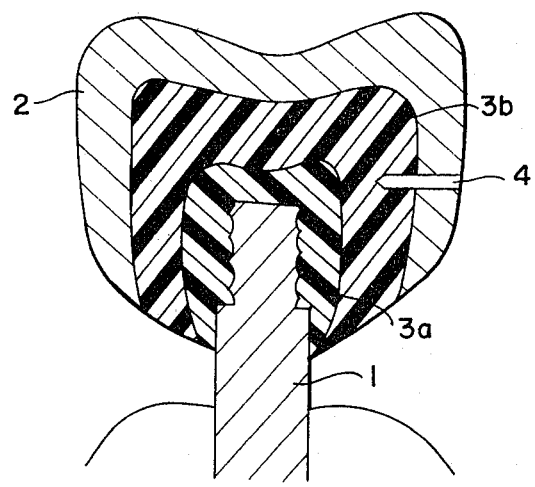
FIG. 2 is an enlarged cross sectional view of the upper structure of the implant artificial denture shown in FIG. 1.

FIG. 1 is a longitudinal cross sectional view of an implant artificial denture implanted in a jaw, showing an embodiment of the present invention. FIG. 2 is an enlarged cross sectional view of the upper structure of the implant artificial denture shown in FIG. 1. FIG. 3 is an enlarged cross sectional view of the upper structure of the implant artificial denture showing another embodiment of the present invention.

In FIGS. 1 to 3, 1 is an intra-ossal implant, 2 is a crown of tooth, 3, 3a, or 3b is an elastic material respectively, 3a showing a soft elastic material and 3b showing a rigid elastic material, 4 is a spirally-screwed pin for fixing the crown of tooth to the elastic material, 5 is a stopper ring for fixing the elastic material to the implant, 6 is the gum and 7 is the jaw.

The intra-ossal implant 1 in FIG. 1 is provided with a screw thread to be screwed into a threaded hole drilled in the jaw on the root section thereof, and also provided with a screw thread corresponding to a threaded hole drilled in the soft elastic material 3a on the head thereof. It may also have a prism section for applying a screw driver thereto as well as a collar section horizontally projecting to be fitted in the jaw.

It may be of different shapes, for example, one not having a collar, one having a different joining structure of the elastic material, or one a plate-like root section buried in a groove drilled in the jaw and a single or a plurality of head thereof.

In FIGS. 1 to 3, the elastic material 3 is composed of two layers, that is, a soft elastic material with a high coefficient of elasticity, fitted over the head of the implant, and a rigid elastic material 3b with a low coefficient of elasticity, fitted over the soft elastic material.

The elastic material 3 may be provided as a uniform single layer construction, preferably a multi-layer construction comprising a plurality of elastic materials with different coefficients of elasticity in order to absorb a multi-directional pressure or shock applied thereto and to prevent the crown of tooth as rigid material from being distorted.

Examples of the method applicable of fitting detachably the soft elastic material over the head of the intra-ossal implant 1 include one of screw fitting, one of fitting in by providing with projections, one of fixing with a spirally screwed pin, and the like.

In the example shown in FIGS. 1 and 2, the soft elastic material 3a with a threaded hole formed by drilling is fitted by screwing over the head of the implant with a screw thread corresponding thereto.

In the example shown in FIG. 3, an annular groove is fitted appropriately on the head of the implant to which the soft elastic material is fitted to fit a stopper ring 5 thereto and the soft elastic material with a drilled cavity corresponding thereto is fitted therein.

The crown of tooth 2 may be fitted detachably over the elastic material 3 fitted over the implant by fitting therein with projections or a stopper ring, and by fixing with a spirally screwed pin.

As shown in FIGS. 1 to 3, the crown of tooth 2 is preferably fitted over the elastic material 3 by drilling a threaded hole extending to the elastic material 3 but not to the head of the implant to fix with a spirally screwed pin 4.

Figure 4:
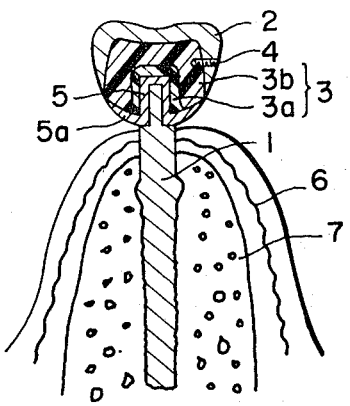
FIG. 4 is a longitudinal cross sectional view of an implant artificial denture showing another embodiment of the present invention.
Figure 5:
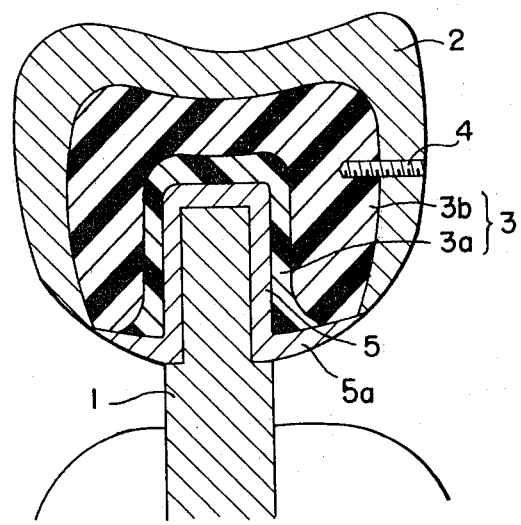
FIG. 5 is an enlarged cross sectional view of the upper structure of the implant artificial denture shown in FIG. 4.

FIG. 4 is a longitudinal cross sectional view of an implant artificial denture showing another embodiment of the present invention, and FIG. 5 is an enlarged cross sectional view of the upper structure of the implant artificial denture shown in FIG. 4.

In FIG. 4, 1 is an intra-ossal implant, 2 is a crown of tooth, 3 is an elastic material including a soft elastic material 3a and a rigid elastic material 3b, 4 is a spirally screwed pin, 5 is a receiver, 5a is a supporting collar section of the receiver 5, 6 is the gum and 7 is the jaw.

The intra-ossal implant 1 is implanted in the jaw 7, over the head of which the receiver 5 is fitted. The receiver 5 may be fitted over the head of the intra-ossal implant 1 by fitting firmly, by screw fitting, or by fixing with cement. The receiver 5 is provided with the supporting collar section 5a integrally fitted thereto in such a manner that the supporting collar section 5a is shaped to be fitted over the soft elastic material 3a and the rigid elastic material 3b, and the rigid elastic material 3b is fitted over the soft elastic material 3a.

The soft elastic material 3a may be fitted to the receiver 5 by fixing with an elastic adhesive or with supporting projections provided on the surface of the receiver 5.

Thus the soft elastic material 3a is surrounded completely by the receiver 5 and the rigid elastic material 3b to be isolated from the environment in the cavity of the mouth.

The rigid elastic material 3b may be fitted firmly over the soft elastic material 3a by the action of their appropriate rigidity and elasticity.

The crown of tooth 2 may be fitted over the rigid elastic material 3b by fitting firmly, by fixing with adhesive, or preferably in such a manner that a threaded hole is drilled passing through the crown of tooth 2 and the rigid elastic material 3b in the direction from inner side to center of the denture, and a spirally screwed pin is screwed thereto to prevent the crown of tooth 2 from falling off the rigid elastic material 3b.

Figure 6:
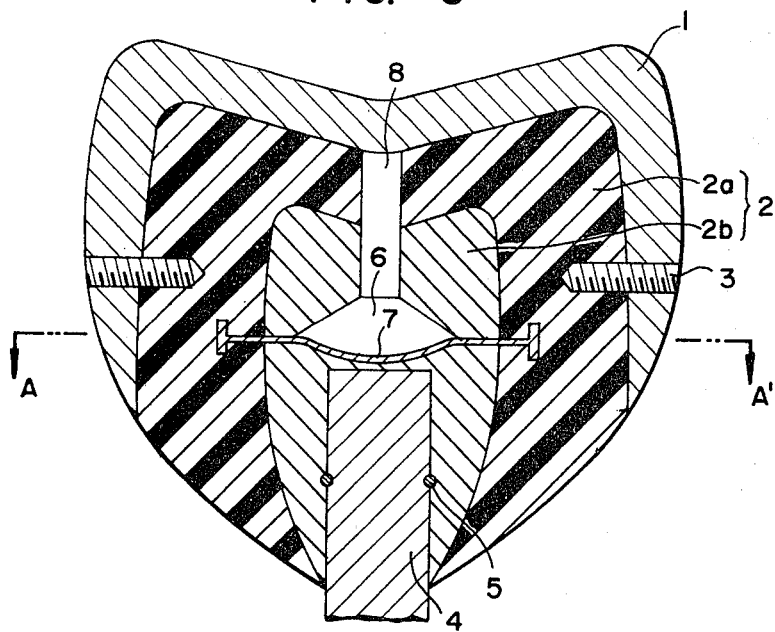
FIG. 6 is a longitudinal cross sectional view of the upper structure of an implant artificial denture incorporating therein a chewing load limit sensing device showing an embodiment of the present invention.
Figure 7:
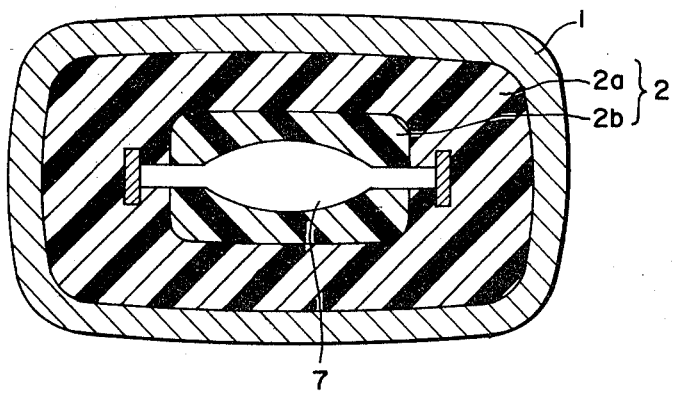
FIG. 7 is a cross sectional view taken along the plane of section line A—A' of FIG. 6.

FIG. 6 is a longitudinal cross sectional view of the upper structure of an implant artificial denture incorporating therein a chewing load limit sensing device showing an embodiment of the present invention, and FIG. 7 is a cross sectional view taken along the plane of section line A—A' of FIG. 6.

In FIG. 6 the crown of tooth 1 is fitted over the elastic material 2 comprising the soft elastic material 2a and the rigid elastic material 2b, and is fixed thereto by means of a spirally screwed pin 3. The elastic material 2 is fitted over the head of the intra-ossal implant 4, and is fixed thereto by means of the stopper ring 5 fitted to the head of the implant.

An elastic diaphragm 7 is incorporated in the elastic material 2 spaced within a certain limit from the tip of the head of the implant, and the everting portion thereof is located within the tympanic cavity 6 comprising a cavity necessary for the temporary eversion thereof. In the elastic material 2, an interstice 8 passing through the tympanic cavity 6 may be provided.

Figure 8:
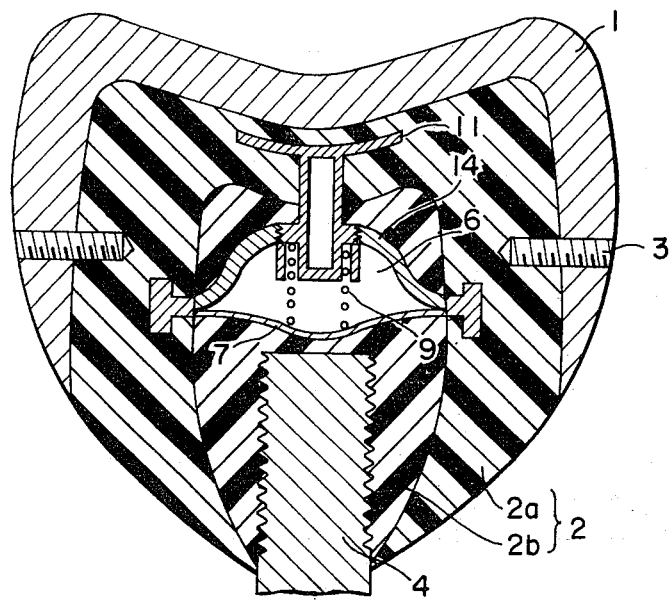
FIG. 8 is a longitudinal cross sectional view of the upper structure of an implant artificial denture incorporating therein a chewing load limit sensing device and showing another embodiment of the present invention.
Figure 9:
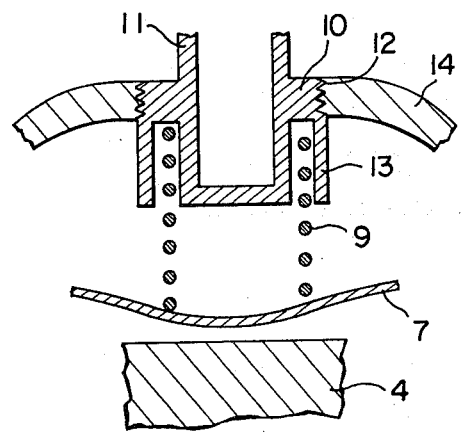
FIG. 9 is a partially enlarged cross sectional view of the upper structure of the implant artificial denture shown in FIG. 8.

FIG. 8 is a longitudinal cross sectional view of the upper structure of an implant artificial denture incorporating therein a chewing load limit sensing device and showing another embodiment of the present invention, and FIG. 9 is a partially enlarged cross sectional view of the upper structure of the implant artificial denture shown in FIG. 8.

In FIG. 8, the crown of tooth 1 is fitted over the elastic material 2 comprising the soft elastic material 2a and the rigid elastic material 2b, and is fixed thereto by means of a spirally screwed pin 3. The elastic material 2 is fitted over the head of the implant 4 and is fixed thereto by screw fitting. The elastic diaphragm 7 is incorporated within the elastic material 2 comprising the soft elastic material 2a and the rigid elastic material 2b spaced within a certain limit from the tip of the head of the implant, and the both ends thereof are fixed in the rigid elastic material 2b. The everting portion of the diaphragm 7 is located within the tympanic cavity 6 comprising a cavity necessary for the temporary eversion thereof, and is shaped to form a gently curved convex surface to the head of the implant 4.

A spring device for the restoration of the diaphragm 7 is fitted between the elastic diaphragm 7 and the back side of the crown of tooth 1 in the axial direction of the implant, which spring device comprises a spring 9, a spring receiver 11 having a spring receiver screw section 10 and a spring bearer 13 both integrally fitted to the head thereof, and a spring receiver bearer 14.

The application of a chewing pressure exceeding a certain limit to the crown of tooth 1 causes the elastic material 2 to push in the direction from the crown of tooth 1 to the head of the implant 4 along the axial direction of the implant, and consequently the everting portion of the diaphragm 7 is pushed toward the tip of the head of the implant, which results in the temporary eversion of the diaphragm 7 to produce a bounding sound. The diaphragm 7 is restored immediately the moment the load exceeding a limit of chewing pressure is released, and the restoration of the original shape of the diaphragm 7 is ensured by providing with the spring device. The spring 9 is held in the axial direction of the implant by means of the spring bearer 13, and the tip thereof is properly pushed on the everting portion of the diaphragm 7. The spring receiver 11 holds out the pressure applied to the spring due to the temporary eversion of the diaphragm 7, and supports the spring 9 together with the spring bearer 13. The spring receiver bearer 14 is connected and fixed to the spring receiver screw section 10 integrally fixed to the spring receiver 11 by means of a screw 12. The portion of the spring receiver excepting the head thereof, the spring bearer 13 and the spring receiver screw section 10, that is, the portion thereof in the vicinity of the crown of tooth 1 may be omitted, if desired.

According to the present invention, the problems causing the drawbacks of the conventional implant artificial denture, such as the dissolution and uptake of the bone as well as the inflammation of tissue in the neighbourhood of the interface between the intra-ossal implant and the jaw tissue due to the chewing and masticatory pressure or shock applied thereto can be solved by fitting the elastic material between the crown of tooth and the intra-ossal implant.

According to the implant artificial denture of the present invention, the exchange of the elastic material and the dental prosthesis can readily be made, and the conditions of the artificial denture can be adjusted depending on the masticatory pressure applied to the portion subjected to operation, the change of the tissue in the region of the implant after the intra-ossal implant was implanted, or the change of the surrounding tissue after using the implant for a long period of time because the elastic material and the crown of tooth are detachable from each other.

According to the present invention, the adjacent healthy teeth need not be injured, and it is usually unnecessary for the implant artificial denture to make the masticatory surface smaller and smoother so that the pressure or shock applied to the dental root may not be so high, and to reduce the masticatory force by other means, ensuring the possibility for complete chewing.

With the receiver of the present invention fitted over the head of the intra-ossal implant for holding out the masticatory and chewing pressure or shock applied to the elastic material, the masticatory and chewing pressure or shock may not only be absorbed more efficiently with smaller amount of elastic material, but also the restoration of the elastic material may be made more effectively after the pressure or shock applied thereto was released, which makes it possible to use the elastic material for a long period of time.

With a soft elastic material with an appropriately high coefficient of elasticity and isolated from the environment in the cavity of the mouth by surrounding it completely with the receiver and the rigid elastic material with an appropriately low coefficient of elasticity, an elastic material usable as the soft elastic material may be selected arbitrarily from a wider range of elastic material.

With the chewing load limit sensing device incorporated in the upper structure of the implant artificial denture, it is possible to ensure to prevent the dissolution and uptake of the bone as well as the inflammation of tissue in the neighbourhood of the interface between the intra-ossal implant and the jaw tissue, and the damage of the implant artificial denture, the surrounding tissue thereof, the jaw joint and the like due to the masticatory and chewing pressure or shock applied thereto.

According to the present invention, by selecting appropriately the elastic material and the chewing load limit sensing device depending on the conditions of the implant artificial denture used, a most suitable combination may be obtained to absorb the pressure or shock applied thereto and to provide a synergistic effect, because the elements of the upper structure of the implant artificial denture are fitted detachably to each other.

What is claimed is:

1. An implant artificial denture, comprising:
   an intra-ossal implant for implantation in a jaw, said implant having a head with an axially outer tip integral therewith;
   an elastic material fitted over substantially all of said head; and
   a prosthetic tooth crown fitted directly over the elastic material but only indirectly over said head due to the presence of said elastic material therebetween;
   said elastic material including a contacting surface shaped to conform with said prosthetic tooth crown and to adhere said elastic material to said prosthetic tooth crown;
   said elastic material being constituted by a construction which is of progressively lower elasticity outwards through the thickness thereof such that said elastic material has a relatively higher coefficient of elasticity distally of said contacting surface and relatively lower coefficient of elasticity proximally of said contacting surface.

2. The implant artificial denture of claim 1, wherein:
   the elastic material constitutes a multi-layer construction comprising a plurality of elastic material layers with respectively different coefficients of elasticity in series.

3. The implant artificial denture of claim 2, wherein:
   the elastic material comprises a soft elastic material layer with an appropriately high coefficient of elasticity with a rigid elastic material layer with an appropriately low coefficient of elasticity, said soft elastic material layer being fitted over the head of the intra-ossal implant, and said rigid elastic material layer being fitted entirely over the soft elastic material layer.

4. An implant artificial denture, comprising:
   an intra-ossal implant for implantation in a jaw, said implant having a head with an axially outer tip integral therewith;
   an elastic material fitted over substantially all of said head; and
   a prosthetic tooth crown fitted directly over the elastic material but only indirectly over said head due to the presence of said elastic material therebetween;
   said elastic material including a contacting surface shaped to conform with said prosthetic tooth crown and to adhere said elastic material to said prosthetic tooth crown;
   a chewing load limit sensing device being incorporated within the elastic material for emitting a warning signal when a pre-selected chewing load is placed on said prosthetic tooth crown.

5. An implant artificial denture, comprising:
   an intra-ossal implant for implantation in a jaw, said intra-ossal implant having a head with an axially outer tip;
   an elastic material fitted over said head of the intra-ossal implant; and
   a prosthetic tooth crown fitted over the elastic material;
   a chewing load limit sensing device is incorporated within the elastic material;
   the chewing load limit sensing device comprising an elastic diaphragm having two ends with an everting portion between them, and a tympanic cavity;
   said elastic diaphragm being incorporated between the head of the intra-ossal implant and the back side of the prosthetic tooth crown in the axial direction of the implant in such a manner that it is fitted in the vertical direction to the implant axis, said two ends thereof being fixed in the rigid elastic material, and the everting portion thereof being shaped to form a gently curved convex surface to the head of the intra-ossal implant and being located within said tympanic cavity, and the top surface of the everting portion of the elastic diaphragm being spaced within a certain distance from said tip of the head of the intra-ossal implant.

6. The implant artificial denture of claim 5, wherein:
   said chewing load limit sensing device further comprises a spring device;
   said spring device comprising a spring, a spring receiver having a spring receiver screw section and a spring bearer both integrally fitted thereto, and a spring receiver bearer;
   said spring device being fitted between the elastic diaphragm and the back side of the prosthetic tooth crown in the axial direction of the intra-ossal implant, said spring being held by the spring bearer;
   an end of the spring being pressed on the back side of the elastic diaphragm;
   said spring receiver bearer being faced to the elastic diaphragm;
   one end of the spring receiver bearer being fixed in the elastic material with a corresponding end of the elastic diaphragm and another end thereof being connected detachably to the spring receiver screw section by means of a screw.

7. The implant artificial denture of claim 5, wherein:
   the chewing load limit sensing device further comprises means providing an interstice passing through the tympanic cavity and leading to the back side of the prosthetic tooth crown.

8. The implant artificial denture according to claim 5, wherein:
   the top surface of the everting portion of the elastic diaphragm is spaced in the range of from 0 to 3 mm from said tip of the head of the intra-ossal implant in the axial direction.

9. The implant artificial denture according to claim 5, wherein:
   the elastic material constitutes a multi-layer construction comprising a plurality of elastic material layers with respectively different coefficients of elasticity in series.

10. The implant artificial denture according to claim 9, wherein:
    the elastic material comprises a soft elastic material layer with an appropriately high coefficient of elasticity and a rigid elastic material layer with an appropriately low coefficient of elasticity, said soft elastic material layer being fitted over the head of the intra-ossal implant, and said rigid elastic material layer being fitted over the soft elastic material layer.

11. The implant artificial denture according to claim 10, wherein:
    said two ends of the elastic diaphragm are fixed in the rigid elastic material.

12. The implant artificial denture according to claim 1, or 5 wherein:
the head of the intra-ossal implant, the elastic material and the prosthetic tooth crown are detachably fixed to each other.

13. The implant artificial denture according to claim 1, or 5 wherein:
the elastic material is fitted detachably over the head of the intra-ossal implant by providing therewith a screw thread on the head of the intra-ossal implant to which the elastic material is fitted and by screwing thereto the elastic material via a correspondingly threaded hole provided therein.

14. The implant artificial denture according to claim 1, or 5, wherein:
the elastic material is fitted detachably over the head of the intra-ossal implant by providing appropriately therewith an annular groove on the intra-ossal implant to which the elastic material is fitted to fit a stopper ring thereto, and by fitting therein the elastic material with a drilled cavity corresponding to the head of the intra-ossal implant.

15. An implant artificial denture, comprising:
an intra-ossal implant for implantation in a jaw, said intra-ossal implant having a head with an axially outer tip integral therewith;
a receiver fitted over said head of the intral-ossal implant;
an elastic material fitted over the receiver; and
a prosthetic tooth crown fitted over the elastic material;
said receiver having a supporting collar section integrally fitted thereto;
said supporting collar section extending outwards at the bottom of said head and being shaped to be fitted tightly under the elastic material;
said prosthetic tooth crown being fitted over said head of the intra-ossal implant through said receiver and said elastic material successively without being fitted directly over said head and without being fixed directly to said head and said supporting collar section;
said prosthetic tooth crown further being fitted directly over said elastic material; said elastic material including a contacting surface shaped to conform with said prosthetic tooth crown so as to adhere said tooth crown to said elastic material.

16. The implant artificial denture according to claim 15, wherein:
said receiver is fitted over a bottom section of said head, and said elastic material is fitted over a top section of said head and over said receiver.

17. The implant artificial denture according to claim 15, wherein:
said supporting collar section extends transversally outward and has an outer surface which is gently convexly curved in the axially inner direction and is arranged so that when a section of the intra-ossal implant is planted, said outer surface bears thereagainst.

18. The implant artificial denture according to claim 15, wherein:
the head of the intra-ossal implant, the receiver, the elastic material and the prosthetic tooth crown are detachably fitted to each other.

19. The implant artificial denture according to claim 18, wherein:
the receiver is fitted over the head of the intra-ossal implant by screw fitting.

20. The implant artificial denture according to claim 18, wherein:
the elastic material is fitted to the receiver by fixing with supporting projections provided on the receiver.

21. The implant artificial denture according to claim 15, wherein:
the receiver is fitted over the head of the intra-ossal implant by fixing with cement.

22. The implant artificial denture according to claim 15, wherein:
the elastic material is fitted to the receiver by fixing with an elastic adhesive.

23. The implant artificial denture according to claim 15, wherein:
the elastic material constitutes a multi-layer construction comprising a plurality of elastic material layers with respectively different coefficients of elasticity in series.

24. The implant artificial denture according to claim 23, wherein:
the elastic material comprises a soft elastic material with an appropriately high coefficient of elasticity and a rigid elastic material with an appropriately low coefficient of elasticity, said soft elastic material being fitted over the receiver, and said rigid elastic material being fitted over said soft elastic material.

25. The implant artificial denture according to claim 24, wherein:
the supporting collar section of the receiver is fitted over the entirety of said soft elastic material and is fitted over at least part of said rigid elastic material.

26. The implant artificial denture according to claim 1, 5 or 15, wherein:
the prosthetic tooth crown is fitted over the elastic material and fixed thereto by a threaded hole extending in the direction from the inner side to the center of the denture, said threaded hole passing through the prosthetic tooth crown to reach the elastic material but not to reach the head of the intra-ossal implant, and by a spirally threaded pin screwed into the threaded hole.

27. The implant artificial denture according to claim 1, 5 or 15, wherein:
the elastic material is made of a polymeric material selected from the group consisting of silicone resin, nylon, fluoroplastics, vinyl resin, polyacrylic ester resin, polyolefin plastics, and polyurethane plastics.

28. The implant artificial denture according to claim 1, 5 or 15, wherein:
the elastic material has such a coefficient of elasticity as to compress in the range of from 0.5 to 1 mm during chewing by a human implantee of the implant artificial denture.

29. The implant artificial denture according to claim 1, 5 or 15, wherein:
the elastic material has such a coefficient of elasticity as to compress in the range of from 0.1 to 0.2 mm due to the normal masticatory pressure when in use by a human implantee.

30. The implant artificial denture according to claim 1, 5 or 15, wherein:
the elastic material has such a coefficient of elasticity as to compress in the range of from a volumetric compression of about 1/50 under a pressure of 0.5 kg/cm$^2$ to a volumetric compression of about 1/50 under a pressure of 100 kg/cm$^2$ according to such pressure as is normally applied thereto during chewing by a human implantee of the implant artificial denture.

* * * * *